United States Patent [19]
Lavallee et al.

[11] 4,208,328
[45] Jun. 17, 1980

[54] ALKYL 3,5-DIHYDROXY-4-(2-BENZOTHIAZOLYL)-BENZOATES

[75] Inventors: Francois A. Lavallee, Cleveland Heights; Raymond H. Pritschau, Highland Heights, both of Ohio

[73] Assignee: General Electric Company, Schenectady, N.Y.

[21] Appl. No.: 900,667

[22] Filed: Apr. 27, 1978

[51] Int. Cl.$^2$ ............................................. C07D 277/66
[52] U.S. Cl. ..................................... 548/180; 548/334; 252/301.28; 548/224
[58] Field of Search ........... 260/304 P, 304 R, 307 D; 548/334

[56] References Cited

U.S. PATENT DOCUMENTS 3,294,542  12/1966  Sus et al. ........................ 548/334
3,972,875  8/1976  Smith ............................... 260/304 P

FOREIGN PATENT DOCUMENTS 1545880  12/1969  Fed. Rep. of Germany ...... 260/307 D
1156800  7/1969  United Kingdom ............... 260/307 D

*Primary Examiner*—Donald G. Daus
*Assistant Examiner*—D. B. Springer
*Attorney, Agent, or Firm*—John F. McDevitt; Lawrence R. Kempton

[57] ABSTRACT

A series of solid organic luminescent materials is disclosed comprising the condensation product of a substituted aromatic primary amine with an alkyl ester of a hydroxy aromatic acid having an alkyl group containing up to about 6 carbon atoms. The present organic phosphors can be excited with 3650 Angstrom radiation to provide efficient red color emission. A process for the preparation of these phosphors is also disclosed.

2 Claims, No Drawings

ALKYL 3,5-DIHYDROXY-4-(2-BENZOTHIAZOLYL)BENZOATES

BACKGROUND OF THE INVENTION

Various generally related benzazolyl compounds are known including many which can exhibit luminescence when excited by ultraviolet radiation. For example, U.S. Pat. No. 3,673,202 discloses 2,5-bis(2-benzazolyl) hydroquinones and their derivative which emit blue to near infrared radiation when excited to ultraviolet light. In U.S. Pat. No. 3,723,449, there is also disclosed certain phthalimidomethyl derivatives of 2-(2-hydroxyphenyl) benzothiazole which emit a yellow color radiation upon exposure to ultraviolet light. A process for preparing 2-(2-hydroxyphenyl) benzothiazole which also is an organic phosphor emitting in the green color spectrum when exposed to ultraviolet light is disclosed in U.S. Pat. No. 3,374,649. While the latter phosphor material can be synthesized in efficient yields by said process, it is said not to be as stable as the phthalimidomethyl derivatives previously mentioned, and which derivatives lack appreciable solubility in the commonly employed organic solvents. Additionally, the derivative phosphors disclosed in the aforementioned U.S. Pat. Nos. 3,673,202 and 3,723,449 patents have been found difficult to prepare in high yield by the known methods which generally entail a number of elaborate process steps.

SUMMARY OF THE INVENTION

It has been found, surprisingly, that a novel series of red emitting phosphors can be prepared in efficient yield by a simple condensation process and that said phosphor materials are readily soluble in common organic solvents. Specifically, a new class of red emitting phosphors has been discovered having the formula:

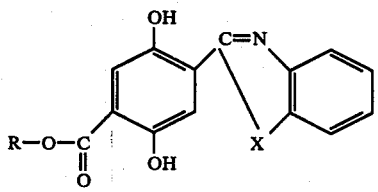

wherein, R=H, CH$_3$ and lower alkyl groups containing up to about 6 carbon atoms, and X=S, O, or NH.

Representative phosphor materials included within the above structural formula which emit efficiently in the red color spectrum when excited with 3650 Angstrom radiation are methyl[3,5-dihydroxy-4-(2-benzothiazolyl)] benzoate and methyl[3,5-dihydroxy-4-(2-benzoxazolyl)] benzoate. The novel process for preparing these phosphor materials comprises heating reaction mixtures of an ortho substituted aromatic primary amine with an alkyl ester of an aromatic acid having an alkyl group containing up to about 6 carbon atoms and proper amounts of a hydroxy aromatic compound and an amine to a temperature sufficient to melt such reactants in an atmosphere inert to said reactants and the products formed therefrom, continuing said heating until the reaction is substantially complete, and separating the red phosphor material from the reaction mixture.

The method of preparation disclosed herein enables interim conversion of one starting material used in the synthesis, namely an alkyl ester of a hydroxy aromatic acid, to be converted to the corresponding aromatic ester of said aromatic acid for direct condensation thereafter with the aromatic primary amine starting material in said reaction mixture to form the desired phosphor. The prior art methods employ either aromatic aldehydes, aromatic acids, or the aromatic esters per se for one starting material in the reaction mixtures as distinct therefrom and which further requires use of relatively expensive reactants or multiple reaction steps. The catalyst system in the present method which overcomes these difficulties is a particular combination of a hydroxy aromatic compound with an amine generally in the ratio of about 5.5/1 down to 1/1 mole of said aromatic compound to said amine. Suitable aromatic hydroxy compounds can be selected from phenol, catechole, 2,4,6 tribromophenol, 2,4,6 trimethylphenol, paraphenyl phenol and hydroquinone. A suitable amine for the catalyst system includes imidazole and 4-dimethyl-aminopyridine. The mole ratio of said amine to the alkyl ester of aromatic acid in the starting mixture for the present synthesis method should also be equal or greater than a number of ester groups being converted to the benzazolyl group in said starting reactant.

DESCRIPTION OF THE PREFERRED EMBODIMENTS

The following examples illustrate preparation of substituted hydroxy benzazolyl phosphors of the present invention having the structural formula above defined wherein the ester substituent is a methyl group such as methyl[3,5-dihydroxy, -4-(2-benzothiazolyl)] benzoate and methyl[3,5-dihydroxy, -4-(2-benzoxazolyl)] benzoate although it is contemplated that ethyl esters, propyl esters and higher carbon esters would provide soluble organic phosphors exhibiting efficient red color emission. In all of said examples, parts and percentages are reported by weight unless otherwise specified.

EXAMPLE 1

The synthesis of 3,5-bis benzothiazolyl hydroquinone is carried out in a suitable reaction vessel including means to heat the reaction mixture as well as provide an atmosphere inert to both reactants and the products formed therefrom. Approximately 5.0 grams dimethyl-(3,6-dihydroxy) terephthalate, 6.8 grams imidazole, 2.0 grams catechole and 9.0 grams ortho-aminothiobenzene are added to said reaction vessel and heated to about 130°–140° C. for at least six hours while purging with dry nitrogen to remove oxygen from the reacting vessel. Said reaction mixture is thereupon cooled to room temperature, and a desired product precipitated from the reaction mixture using a 4/1 volume ratio water to concentrated hydrochloric acid mixture. The separated product is then filtered and washed again with 400 milliliters of deionized water and finally dried under vacuum at about 50°–70° C.

EXAMPLE 2

The same method described in Example 1 is used for synthesis of methyl 3,5-dihydroxy -4-(2-benzothiazolyl) benzoate except that said product is separated from the reaction mixture in a different manner. Accordingly, a starting mixture comprising 5.0 grams dimethyl-(3,6-dihydroxy) terephthalate, 5.5 grams imidazole, 1 gram catechole, and 2.3 grams 2-aminothiobenzene is added to the reaction vessel and heated to 130°-140° C. for 6-17 hours after purging with nitrogen for approximately 15 minutes. The product mixture is then cooled to room temperature and the product removed therefrom by dissolving the soluble phosphor with acetone. The dissolved product is subsequently precipitated out of solution with water and washed thereafter with additional water for purification.

Both above phosphor products exhibited efficient red color emission when exposed to ultraviolet light of 3650 Angstrom wavelength. Accordingly, said products are broadly useful in varied applications including incorporation in various resin compositions such as lacquers or plastics to produce a distinctive colored light. The new class of phosphors has also proven relatively stable to photochemical and oxidation type reactions thereby not experiencing substantial loss of the desired emission characteristics. It will be apparent to those skilled in the art, therefore, that variations in the embodiments above disclosed are possible without departing from the intended scope of the invention as defined in the appended claims.

What we claim as new and desire to secure by United States Letters Patent is:

1. A phosphor having the formula:

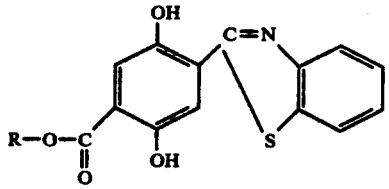

wherein R = lower alkyl groups having up to 6 carbon atoms, said phosphor providing red color emission when excited with 3650 Angstrom radiation.

2. The red phosphor methyl benzoate.

* * * * *

UNITED STATES PATENT AND TRADEMARK OFFICE
CERTIFICATE OF CORRECTION

PATENT NO. : 4,208,328
DATED : June 17, 1980
INVENTOR(S) : Francois A. Lavallee et al It is certified that error appears in the above-identified patent and that said Letters Patent are hereby corrected as shown below:

In column 4, change claim 2 to read:

2. The red phosphor methyl [3,5-dihydroxy, -4-(2-benzothiazolyl)] benzoate.

Signed and Sealed this

Twentieth Day of October 1981

[SEAL]

Attest:

GERALD J. MOSSINGHOFF

Attesting Officer    Commissioner of Patents and Trademarks